(12) United States Patent
Ulrich et al.

(10) Patent No.: US 6,740,508 B2
(45) Date of Patent: May 25, 2004

(54) FERMENTATION-BASED PRODUCTS FROM CORN AND METHOD

(75) Inventors: James F. Ulrich, Highwood, IL (US); Neal Torrey Jakel, Lake Zurich, IL (US)

(73) Assignee: Renessen LLC, Bannockburn, IL (US)

( * ) Notice: Subject to any disclaimer, the term of this patent is extended or adjusted under 35 U.S.C. 154(b) by 32 days.

(21) Appl. No.: 10/369,073

(22) Filed: Feb. 18, 2003

(65) Prior Publication Data

US 2003/0180897 A1 Sep. 25, 2003

Related U.S. Application Data

(63) Continuation-in-part of application No. 10/046,856, filed on Jan. 15, 2002, which is a continuation-in-part of application No. 09/927,836, filed on Aug. 10, 2001, which is a continuation-in-part of application No. 09/637,843, filed on Aug. 10, 2000, which is a continuation-in-part of application No. 09/249,280, filed on Feb. 11, 1999, now Pat. No. 6,313,328.

(51) Int. Cl.$^7$ .................................................. C12P 19/00
(52) U.S. Cl. ........................ 435/72; 435/144; 435/157; 435/161; 435/162
(58) Field of Search .......................... 435/72, 144, 157, 435/161, 162

(56) References Cited

U.S. PATENT DOCUMENTS

| | | |
|---|---|---|
| 3,432,529 A | 3/1969 | Demper |
| 3,519,431 A | 7/1970 | Wayne |
| 3,786,078 A | 1/1974 | Finley et al. |
| 3,909,288 A | 9/1975 | Powell et al. |
| 3,939,281 A | 2/1976 | Schwengers |
| 4,008,210 A | 2/1977 | Steele et al. |
| 4,246,184 A | 1/1981 | Pressick et al. |
| 4,277,411 A | 7/1981 | Yahl |
| 4,310,468 A | 1/1982 | Reiners |
| 4,341,713 A | 7/1982 | Stolp et al. |
| 4,442,034 A | 4/1984 | Suzuki et al. |
| 4,456,556 A | 6/1984 | Grimsby |
| 4,456,557 A | 6/1984 | Grimsby |
| 4,486,353 A | 12/1984 | Matsuzaki et al. |
| 4,495,207 A | 1/1985 | Christianson et al. |
| 4,594,260 A | 6/1986 | Vaqueiro et al. |
| 5,035,910 A | 7/1991 | Jones et al. |
| 5,085,808 A | 2/1992 | Snyder et al. |
| 5,320,669 A | 6/1994 | Lim et al. |
| 5,408,924 A | 4/1995 | Arendt et al. |
| 5,525,746 A | 6/1996 | Franke |
| 5,670,678 A | 9/1997 | Rothbart |
| 5,675,065 A | 10/1997 | Bergquist |
| 5,706,603 A | 1/1998 | Bergquist et al. |
| 5,750,851 A | 5/1998 | Geadelmann et al. |
| 5,851,572 A | 12/1998 | Cook et al. |
| 5,908,940 A | 6/1999 | Lane et al. |

FOREIGN PATENT DOCUMENTS

| | | |
|---|---|---|
| EP | 0623100 B1 | 4/1997 |
| GB | 2269084 A | 2/1994 |
| GB | 2309150 A | 7/1997 |
| WO | WO 94/15483 A1 | 7/1994 |
| WO | WO 95/22598 A2 | 8/1995 |
| WO | WO 98/43473 A1 | 10/1998 |
| WO | WO 99/52376 A1 | 10/1999 |
| WO | WO 00/10404 | 3/2000 |
| WO | WO 00/47702 A1 | 8/2000 |
| WO | WO 01/55283 A1 | 8/2001 |
| WO | WO 02/13624 A1 | 2/2002 |
| WO | WO 02/14459 A2 | 2/2002 |

OTHER PUBLICATIONS

Aguilera et al., "Laboratory and Pilot Solvent Extraction of Extruded High–Oil Corn," *JAOCS*, 1986, 63(2): pp. 239–243, Texas A&M University, College Station, Texas, USA.

Bockisch, Michael, "Fats and Oils Handbook," 1993, pp. 344, 345 & 360–391, Hamburg, Germany.

Midwest Research Institute For the Office Of Air Quality And Planning And Standards, Emission Factor Documentation for AP–42, Section 9.11.1 Vegetable Processing, Final Report, Nov. 1995, p. 2–12, Research Triangle Park, North Carolina, USA.

Watson, "Corn and Corn Improvement" *Marketing, Processing and Utilization*, 3$^{rd}$ Edition, 1988, No. 18 series Agronomy, pp. 917–918, Madison, Wisconsin, USA.

Watson, et al., "Structure and Composition" *Corn: Corn Chemistry and Technology*, 1987, pp. 538–539, St. Paul, Minnesota, USA.

Blessin, "Carotenoids of Corn and Sorghum," *Cereal Chem.*, 59:236–242 (1962).

Blessin et al., "Carotenoids of Corn and Sorghum," *Cereal Chem.*, 40:582–586 (1963).

Grams et al., "Distribution of Tocopherols Within The Corn Kernel," *J. Amer. Oil Chemists Soc.*, 47:337–339 (1970).

Lambert, "High–Oil Corn Hybrids," *Specialty Corns*, pp. 123–145 (1994).

Paulis et al., "Selection of High–Lysine Corns with Varied Kernel Characteristics and Compositions of a Rapid Turbidimetric Assay for Zein," *J. Agr. Food Chem.*, 22:318–323 (1974).

(List continued on next page.)

*Primary Examiner*—Deborah Carr
(74) *Attorney, Agent, or Firm*—Leydig Voit & Mayer, Ltd.

(57) ABSTRACT

Corn oil and corn meal obtained from corn are included in useful products. A method for producing fermentation-based products comprises combining corn meal with water and an enzyme, and mixing the combination with a micro-organism capable of fermenting a carbon source to produce a fermentation-based product. The corn meal is produced by cracking whole corn, conditioning the whole corn and extracting the whole corn to produce corn meal. The corn grain process generally includes the steps of cracking corn grain having a total oil content of from about 3% by weight to about 6% by weight and extracting a corn oil from the cracked corn grain.

19 Claims, No Drawings

OTHER PUBLICATIONS

AOCS Recommended Practice Ba 2b–82 (1997).
AOCS Recommended Practice Ba 4e–93 (1999).
AOCS Recommended Practice Ba 6–84 (1997).
AOCS Recommended Practice Ba 3–38 (1997).
AOCS Recommended Practice Ca 5a–40 (1997).
AOCS Official Method Ca 12–55 (1997).
AOCS Official Method Cc 13b–45 (2000).
Standard Analytical Methods of the Member Companies of the Corn Refiners Association, Inc., Standard 6–3–57 (1986).
XP–002199802, DuPont Quality Grains (1996).

FERMENTATION-BASED PRODUCTS FROM CORN AND METHOD

The present application is a continuation-in-part of copending U.S. patent application Ser. No. 10/046,856, filed Jan. 15, 2002, which is a continuation-in-part of copending U.S. patent application Ser. No. 09/927,836, filed Aug. 10, 2001, which was a continuation-in-part of copending U.S. patent application Ser. No. 09/637,843, filed Aug. 10, 2000, which was a continuation-in-part of application Ser. No. 09/249,280, filed Feb. 11, 1999, now U.S. Pat. No. 6,313,328 the entire disclosures of which are hereby incorporated by reference.

FIELD OF THE INVENTION

The present invention relates to methods of forming products derived from oil and meal extracted from corn which preferably has an oil content of about 3% by weight to about 6% by weight.

BACKGROUND OF THE INVENTION

Corn, *Zea mays* L., is grown for many reasons including its use in food and industrial applications. Corn oil and corn meal are two of many useful products derived from corn.

Commercial processing plants utilizing conventional methods for extracting corn oil from conventional corn separate the corn seed into its component parts, e.g., endosperm, germ, tipcap, and pericarp, and then extract corn oil from the corn germ fraction. Corn germ produced by wet or dry milling is processed either by pressing the germ to remove the oil or by flaking the germ and extracting the oil with a solvent. In both processes, because the germ was separated from the remainder of the kernel, many or all of the valuable components of the endosperm fraction are absent from the oil.

During dry milling, the corn kernel after removal of the germ is ground into flour (i.e., "meal") and processed without separating the remaining various components of the grain. The milled products, i.e. grits, meal and flour, are then subjected to heat treatments during processing.

In the wet milling process, corn is placed in large steep tanks to be soaked for 2 to 3 days in a mixture of warm water and sulfur dioxide or dilute sulfuric acid. The steeping facilitates the separation of the grain into its component parts (i.e., germ, fiber, starch and gluten (protein)). The germ is then separated out. Similarly, fibrous materials may be screened off and the starch and protein are separated using density differences. Often, further milling is needed to separate out the starch and protein.

A corn-based feed product known as hominy feed is obtained from the dry milling process and is a mixture of corn bran, corn germ, and endosperm, and has a minimum of about 4% by weight oil. Several steps including cracking, grinding, sieving, and blending are required to manufacture hominy feed and the resulting particle size of hominy feed is small relative to meal made by the extraction method described herein.

Industry and health advocates are continually in search of more economical or nutritious products derived from corn. Thus, there exists a need for improved products derived from corn oil and corn meal.

BRIEF SUMMARY OF THE INVENTION

Finished products containing corn oil and/or corn meal obtained from conventional corn include, for example, cooking oil, animal feed, aquaculture feed, paper and paper products, numerous food products such as salad dressings, extruded and/or puffed snack foods, products containing corn sweeteners, cereals, chips, puddings, candies, and breads.

One aspect of the invention provides a nutritious animal feed comprising the corn meal remaining after extraction of oil from corn. Such corn typically has oil content of from about 3% by weight to about 6% by weight. The animal feed can comprise other nutritious products such as vitamins, minerals, seed-derived meal, meat and bone meal, salt, amino acids, feather meal, and many others used in the art of feed supplementation. Further, meal prepared using whole corn may be blended with the meal of the present invention. The animal feed composition can be tailored for particular uses such as for poultry feed, swine feed, ruminant feed such as cattle feed, equine feed, aquaculture feed, pet food and can be tailored to animal growth phases. Particular embodiments of the animal feed include growing broiler feed, swine finishing feed, cattle feed, and poultry layer finishing feed. Feed products can be made with the extracted corn meal that will have a higher relative percentage of protein and lower relative percentage of oil than similar products produced having conventional corn milling procedures.

In another embodiment, the method of processing corn includes an extracting step wherein flaked corn grain is pressed to extract an oil. Alternatively, the flaked corn grain is subject to solvent-based oil extraction. Solvents used to extract miscible or soluble substances from the flaked grain included one or more of the following: any of the hexanes, isoproplyl alcohol, supercritical $CO_2$ and ethyl alcohol. Extracting steps can produce a miscella and a corn meal.

In one preferred embodiment, the whole corn grain to be processed into oil and meal has an oil content of from about 3% by weight to about 6% by weight. Preferably, this corn grain has a fiber content of about 2%, a starch content of about 65%, and a total protein content of at least about 7% by weight, at least about 9% by weight, at least about 11% by weight, or from about 7% by weight to about 20% by weight. Also, preferably, the whole corn grain has a total lysine content of at least about 0.15% by weight, at least about 0.5% by weight, or from about 0.15% by weight to about 2.0% by weight. The whole corn grain to be processed also preferably has a total tryptophan content of at least about 0.03% by weight, at least about 0.20% by weight, or from about 0.03% by weight to about 2.0% by weight. In producing the desired meal, the whole corn grain can either be cracked and then flaked or may be flaked without cracking.

Preferably, the flaked or cracked and flaked corn is subjected to an oil extraction process such as solvent extraction, hydraulic pressing, expeller pressing or aqueous and enzyme extraction. Following oil extraction, a corn meal is preferably produced which has a fiber content of about 3% by weight, a starch content of about 65% by weight, and a protein content of about 9% by weight, at a moisture content of about 12% by weight. The resultant meal also preferably has a meal fat content of from about 0.2% by weight to about 2.0% by weight.

Another aspect of the invention provides a method of using extracted corn meal in an animal feed ration comprising the step of: 1) providing an extracted corn meal prepared by at least flaking whole corn and extracting the flaked corn to remove a portion of the corn oil therefrom; and 2) including the extracted corn meal in an animal feed ration.

Yet another aspect of the invention provides a method of using an extracted corn oil in a food product comprising the steps of: 1) providing an extracted corn oil obtained by at least flaking whole corn to form flaked corn and extracting the flaked corn to remove a portion of the corn oil therefrom and form the extracted corn oil; and 2) including the extracted corn oil in a food product.

Still another aspect of the invention provides a method of using extracted corn oil as a feedstock in an oil refining process. The method comprises the steps of: 1) providing an extracted crude corn oil obtained by at least flaking whole corn to form flaked corn and extracting the flaked corn to remove a portion of the corn oil therefrom and form the extracted crude corn oil; and 2) including the extracted crude corn oil in a raw material stream of an oil refining process.

The miscella remaining after extraction is preferably desolventized to produce a corn oil. The corn oil preferably has a phosphorus content of less than about 800 parts per million, a free fatty acid content of less than about 0.5% by weight and/or a neutral oil loss of less than about 3% by weight.

A preferred embodiment also provides a method of obtaining corn oil and solvent extracted corn meal from corn. Preferably, the corn has an oil content of from about 3% by weight to about 6% by weight. The method provides steps of: 1) tempering the corn; 2) cracking the tempered corn; 3) conditioning the cracked corn; 4) flaking the cracked and conditioned corn; 5) extracting the flaked corn; and 6) removing the solvent from both the corn oil and solvent extracted corn meal. The method provides a greater overall content of corn oil and concentrates the proteins in the meal. Moreover, solvent extractable pigments are removed from the solvent extracted corn meal.

Another aspect of the invention provides a corn oil-based product comprising corn oil obtained by extraction of whole corn or at least the endosperm and germ of corn. Preferably, the whole corn has an oil content of from about 3% by weight to about 6% by weight. The corn oil-based product can comprise other components such as vinegar, spices, vitamins, salt, hydrogen (for forming hydrogenated products), and water. The corn oil used in the products of the invention will generally contain a higher proportion of beta-carotene, xanthophylls or tocotrienol than similar products made with corn oil obtained from corn employing conventional wet or dry milling methods. The corn oil, used in the products of the invention, is generally produced by exposing the entire corn grain, the cracked corn grain or the flaked corn grain to extraction without separation of the germ from the endosperm. Therefore, the solvent-extractable nutrients present in the endosperm are extracted into the corn oil that has been extracted from the germ and endosperm. Products that can be made with the oil prepared as described herein include, but are not limited to, salad dressings, cooking oils, margarines, spray-coated food or feed products, breads, crackers, snack foods, lubricants, and fuels.

In another embodiment of the present invention, whole corn, preferably having an oil content of from about 3% by weight to about 6% by weight, is process by steps including cracking, conditioning, flaking and extraction with a solvent. Preferably, oil is also extracted by subjecting the flaked corn grain to a solvent-based extraction process, hydraulic pressing and/or expeller pressing or aqueous and/or enzyme extraction processes. Solvents used to extract miscible or soluble substances from the flaked grain include all forms of commercially available hexanes, isopropyl alcohol, ethanol, supercritical carbon dioxide or mixtures thereof. Preferably the corn oil miscella is refined by additional processing.

Another aspect of the invention provides various methods of forming extracted blended meals. A first embodiment of this aspect of the invention provides a method of forming an extracted blended meal comprising an extracted meal obtained from corn and one or more other oilseed meals such as soy, sunflower, canola, or cottenseed, the method comprising the step of: 1) combining corn grain and one or more other oilseed grains to form a grain mixture; and 2) subjecting the grain mixture to flaking and an extraction process to remove oil therefrom and form the extracted blended meal.

A further blended meal embodiment provides a method comprising the steps of: 1) combining a cracked and conditioned corn with another cracked and conditioned oilseed to form a conditioned mixture; 2) flaking the conditioned mixture to form a flaked mixture; and 3) subjecting the flaked mixture to an extraction process to remove oil therefrom and form the extracted blended meal.

In addition, the present invention provides a method of producing fermentation-based products from corn meal. Such fermentation-based products include ethanol and citric acid. The method comprises 1) combining an enzyme, water, and a corn meal obtained by cracking whole corn, conditioning the cracked corn and extracting an oil from the conditioned corn by solvent extraction to leave the corn meal; 2) incubating the combination; and 3) mixing the combination with a micro-organism capable of fermenting a carbon source to produce fermentation-based products. The enzyme is any enzyme suitable for fermentation of corn, including an amylase, a protease, a cellulase, an esterase and a liginase. The grain of the whole corn typically has a total oil content of from about 3% by weight to about 6% by weight. The whole corn can be optionally tempered and/or conditioned in order to obtain the corn meal.

A still further blended meal embodiment provides a method comprising the steps of: 1) combining a cracked, conditioned and flaked corn with a cracked, conditioned and flaked other oilseed to form a flaked mixture; and 2) subjecting the flaked mixture to an extraction process to remove oil therefrom and form the extracted blended meal.

In another blended meal extracted corn meal is combined with one or more extracted other oilseed meals to form a blended meal, wherein the extracted corn meal has been obtained by at least flaking and extracting corn to form the extracted corn meal.

In each method, where appropriate, an optional drying step may be introduced to reduce the barrier that arises when water present in either the cracked or flaked corn impedes solvent extraction by water-immiscible solvents.

Another aspect of the invention provides the use of a corn meal in an animal feed or human food, wherein the corn meal is obtained after extraction of corn oil from whole kernels of corn having an oil content of from about 3% by weight to about 6% by weight.

Yet another aspect of the invention provides the use of a corn oil in an animal feed or human food, wherein the corn oil is obtained by extraction from whole kernels of corn having an oil content of from about 3% by weight to about 6% by weight.

Still another aspect of the invention provides a method of using extracted corn oil as an ingredient in cosmetic applications. The method comprises the steps of: 1) providing an extracted crude corn oil obtained by at least flaking whole corn to form flaked corn and extracting the flaked corn to remove a portion of the corn oil therefrom and form the extracted crude corn oil; and 2) including the extracted crude corn oil in a cosmetic product. These types of cosmetics include but are not limited to lipstick and eyeliner.

Other aspects of the invention provide corn oil-containing and/or corn meal-containing products made by the processes described herein.

Unless otherwise defined, all technical and scientific terms and abbreviations used herein have the same meaning as commonly understood by one of ordinary skill in the art to which this invention pertains. Although methods and materials similar or equivalent to those described herein can be used in the practice of the present invention, suitable methods and materials are described below without intending that any such methods and materials limit the invention described herein. All patents publications and official analytical methods referred to herein are incorporated by reference in their entirety. Additional features and advantages of the invention will be apparent from the following description of illustrative embodiments of the invention and from the claims.

DETAILED DESCRIPTION OF THE INVENTION

Corn oil can be rapidly and efficiently extracted on a commercial-scale from corn grain by optionally cracking and then conditioning, and flaking the corn grain and extracting a corn oil. In one preferred embodiment, corn grain useful in the oil processing method of the invention has a total oil content of from about 3% by weight to about 6% by weight. Suitable flaking equipment and methods include conventional flaking equipment and methods used for flaking soybean and other similar oilseed types. Suitable extracting equipment and methods may include conventional methods used for extracting oil from soybean flakes and other similar oilseed types.

Corn harvested from any of several different types of corn plants is useful in the invention. These types of corn plants are, for example, hybrids, inbreds, transgenic plants, genetically modified plants or a specific population of plants. Enhanced extracted meals can be made by subjecting corn to the extraction process described herein. Useful corn grain types include, for example, flint corn, popcorn, flour corn, dent corn, white corn, and sweet corn that are amenable to flaking.

As used herein, the terms "whole kernel" or "whole corn" mean a kernel that has not been separated into its constituent parts, e.g. the hull, endosperm, tipcap, pericarp, and germ have not been purposefully separated from each other. The whole corn may or may not have been ground, crushed, cracked, flaked, or abraded. Purposeful separation of one corn constituent from another does not include random separation that may occur during storage, handling, transport, crushing, flaking, cracking, grinding or abrading. A purposeful separation of the constituent part is one wherein at least 50% of one constituent, e.g., germ, has been separated from the remaining constituents.

Suitable corns used as a raw material for preparing the corn oil and corn meal used in the invention have the general nutrient profiles as shown in Table 1. Amounts are expressed on an "as is" or "as fed" moisture level. Protein, oil, and starch levels can vary in a number of possible combinations in the whole corn used as a raw material for meal and oil of the invention. Acceptable amounts of moisture, oil, protein and starch are illustrated in Table 1.

TABLE 1

| Component | Amount Sample 1 (weight %) | General Amount (weight %) |
| --- | --- | --- |
| Moisture | 14 | 5–25 |
| Oil | 3.6 | 3–6 |
| Protein | 7.8 | 5–10 |
| Starch | 72.6 | 50–80 |
| Lysine | 0.26 | 0.15–2.0 |
| Tryptophan | 0.082 | 0.03–2.0 |

Other suitable properties for preferred corn suitable as a raw material are set forth in Table 2. The amounts listed in Table 2 are expressed on an "as is" or "as fed" moisture level. The amounts shown in Table 2 are exemplary for a corn grain having 3% by weight to 6% by weight oil and 7.5% by weight protein.

TABLE 2

| Component | General Amount (weight %) |
| --- | --- |
| Ash | 0.1–4.0 |
| Lysine | 0.15–1.0 |
| Tryptophan | 0.03–1.0 |
| Methionine | 0.13–1.0 |
| Total Sulfur Amino Acids | 0.23–1.85 |
| Valine | 0.2–1.8 |
| Isoleucine | 0.08–1.36 |
| Arginine | 0.11–1.88 |
| Threonine | 0.08–1.3 |
| Leucine | 0.52–4.12 |
| Histidine | 0.07–1.08 |
| Phenylalanine | 0.22–1.76 |
| Alanine | 0.17–2.80 |
| Aspartic | 0.37–2.96 |
| Cystine | 0.11–0.88 |
| Glutamic | 0.47–7.6 |
| Glycine | 0.11–1.84 |
| Proline | 0.21–3.44 |
| Tyrosine | 0.02–0.54 |
| Serine | 0.1–1.81 |

The yellow #2 corn is generally subjected to an extraction process as described herein to provide the corn oil and corn meal to be included in the finished products of the invention. The "finished product" may be the resulting oil or meal itself or it may refer to a product made by combining the corn oil and/or corn meal of the invention with a variety of other ingredients. The specific ingredients included in a product will be determined according to the ultimate use of the product. Exemplary end uses of the finished products include feed including animal feed, raw material for chemical modification, biodegradable material, blended food product, edible oil, cooking oil, lubricant, biodiesel, snack food, cosmetics, and fermentation process raw material. Products incorporating the meal described herein also include complete or partially complete swine, poultry, and cattle (or other ruminant) feeds, pet foods, and human food products such as extruded snack foods, breads, as a food binding agent, aquaculture feeds, fermentable mixtures, food supplements, sport drinks, nutritional food bars, multivitamin supplements, diet drinks, and cereal foods. Products incorporating the starch described include, e.g., cardboard, paper products and industrial materials.

Important to note is that starting with a single corn type (e.g., 4% by weight oil and 7.5% by weight protein), more than one corn meal type may be produced depending on the end product nutritional requirements by the process of the invention. The significance of this flexibility relates to the nutrient density within feed products and to dietary requirements of animals. One significant advantage of the use of the extraction process for processing corn is that an extracted corn meal can be made to have a specific oil level depending on the extent of oil extraction. Once the oil is removed from the flakes, the remaining corn meal has a nutrient density for protein, amino acids, and other nutrients not removed by the process, greater or different than normal corn grain and greater than that of the starting corn, e.g., greater than 7.5% by weight protein.

According to one extraction process used in preparing the corn oil and corn meal as described herein, whole grain corn, preferably containing from about 3% by weight to about 6% by weight oil, is optionally tempered, optionally cracked, and then conditioned and flaked. After flaking, the flaked corn is extracted as described herein.

The moisture content of the grain can affect the flaking process. It may be necessary for the moisture of the corn grain to be increased by about 1% to about 15% before flaking the seed. Optimizing the grain moisture content to facilitate efficient processing is within the knowledge of those of ordinary skill in the art.

The grain corn is optionally tempered before the conditioning and extracting process. As used herein, the term "tempering" is used interchangeably with the terms "heat soaking" or "steaming" and is a step undertaken to uniformly distribute moisture through the entire corn kernel. Any tempering method known in the art is acceptable. In general, the corn is steeped in an appropriate amount of water for any suitable length of time, such as at least 20 minutes, preferably at least 4 hours more, more preferably at least 6 hours, even more preferably at least 12 hours, or most preferably at least 24 hours. After the corn has steeped for the desired length of time, its moisture content is retested. The corn may be stored for short periods of time, but is preferably processed within 24 hours of tempering and most preferably processed immediately.

Whole grain corn is also optionally cracked. In a preferred embodiment, the whole corn is cracked after tempering yet before conditioning. The corn may be cracked by passing the whole grain corn between two rollers with corrugated teeth spinning toward each other spaced by a defined gap, and/or passing through a grind mill where a rotating toothed disk spins at an adjustable distance from a stationary disk, and/or the use of a hammermill where two rotating metal "hammer" like devices spinning next to one another. Methods for cracking corn or seeds are described in Watson, S. A. & P. E. Ramstad, ed. (1987, Corn: Chemistry and Technology, Chapter 11, American Association of Cereal Chemist, Inc., St. Paul, Minn.), the disclosure of which is hereby incorporated by reference in its entirety. A "cracked" corn is a corn that has undergone the above-described cracking process.

Regardless of whether cracking occurs, the corn is conditioned using methods known to those of ordinary skill in the art and/or methods described herein. As used herein, the term "conditioning" refers to a process by which the corn kernel is softened or plasticized to render it more pliable and amenable to the flaking and extraction processes. Conditioning may include the addition of steam (saturated and/or non-saturated steam) and/or water to the corn. This is done by, for example, the use of a steam jacketed screw conveyor.

The corn grain is then flaked to any appropriate useful size. As used herein, the term "flaking" refers to a process by which corn grain is passed one or more times through flaking rollers to produce flakes. The flaked corn may have a final flake thickness of about 0.01 inches to about 0.03 inches (~0.25 mm to 0.75 mm) or preferably about 0.02 inches (0.50 mm), although other thicknesses may also be used. Useful flake thickness may depend on external limiting parameters such as the oil content of the corn, the moisture content, the corn type, e.g., dent or flint, and the oil extractor type. Suitable methods for flaking whole corn are detailed herein and in D. R. Erickson, Practical Handbook of Soybean Processing Utilization (1995, AOCS Press), the entire disclosure of which is hereby incorporated by reference. Suitable flaking methods also include those known to those of ordinary skill in the art of oilseed processing.

After the corn is tempered, cracked and/or conditioned and flaked, the flaked corn is subjected to an extraction process to extract oil to form an extracted corn meal (ECM). Corn oil is extracted from flaked grain by one or more extraction steps using any extraction method. Generally, substantially all of the oil is extracted in a single extraction process. Useful extraction methods include solvent extraction, continuous solvent extraction, hydraulic pressing, expeller pressing, aqueous and/or enzyme extraction. Useful solvents for solvent extraction include, for example, all forms of commercially available pentane, hexanes, isopropyl alcohol, ethanol, supercritical carbon dioxide, combinations thereof, and other similar solvents. For example, corn oil can be extracted from flaked corn using a hexane-based solvent extractor. Solvent extractors can include both percolation and immersion type extractors. In a preferred embodiment, a continuous solvent extraction process allows the flaked corn to remain in contact with the solvent for at least 10 minutes, preferably at least 30 minutes, more preferably at least 60 minutes, and most preferably at least 90 minutes.

Materials removed from solvent-based extractors include wet flakes and miscella. A miscella is a mixture of extracted oil and solvent. The wet flakes are the materials that remain after some or all of the solvent-soluble material has been extracted. Wet flakes also contain a quantity of solvent. Solvent is reclaimed from both the miscella and wet flakes using methods such as rising film evaporation, or drying, and raising the temperature using equipment such as flash tanks and/or de-solventiser/toasters. For example, heat is applied to the wet flakes or miscella under atmospheric pressure, under elevated pressure, or under vacuum to evaporate the solvent. The evaporated solvent is then condensed in a separate recovery system, and optionally dewatered and recycled to the extractor.

Desolventized miscella is commonly termed crude oil, which can be stored and/or undergo further processing. Crude oil can be refined to produce a final oil product. Methods for refining crude oil to obtain a final oil product are known to those of ordinary skill in the art. Hui (1996) provides a thorough review of oils and oilseeds (Bailey's Industrial Oil and Fat Products, Fifth Ed., Vol. 2, Wiley and Sons, Inc., New York). Chapter three of Hui (pp. 125–158), the disclosure of which is hereby incorporated by reference, specifically describes corn oil composition and processing methods. Crude oil isolated using the flaking methods described herein is of a high quality but can be further purified as needed using conventional oil refining methods.

In one embodiment, the present invention relates to a method of recovering lighter particles, such as fines, during the processing of corn. As used herein, the term "fines" means any particle of the corn process that passes through a #18 sieve having a 1.00 mm opening as defined in ASTM E-11 specifications. The recovery of the particles may occur before, after, or during any step in the process, such as during the moisture removal step, during the cracking step or before or after the flaking process. In general, fines are recovered by passing a current of gas (e.g., air, nitrogen, argon) over the corn at a suitable velocity and direction such that smaller and lighter particles are carried away in the stream, leaving behind larger, heavier particles. Alternatively, lighter particles can be separated from heavier particles using a liquid (e.g., water, oil, process water) spray. The liquid is applied broadly enough to physically eliminate the lighter, airborne particles. The liquid spray can include components that add value to the end product, such as vitamins, minerals, enzymes, and combinations thereof. In addition, the liquid spray can further comprise a caustic liquid. Regardless of the separation method, these fine particles can be captured or recovered by any method known in the art such as using a baghouse. Preferably, the recovered lighter particles can be reintroduced into starch-containing product streams for the recovery of starch. Additionally the fines may be sold as an animal feed.

Corn endosperm includes some valuable components such as carotenoids, lutein, and zeazanthin. Carotenoids in grains are classified into two general groups, the carotenes and the xanthophylls. The carotenes are important because they are vitamin A precursors. Blessin et al. (*Cereal Chemistry*, 40, 582–586 (1963)) found that over 90% of the carotenoids, of which beta-carotene is predominant, are located in the endosperm of yellow #2 corn and less than 5% are located in the germ. Vitamin A is derived primarily from beta-carotene.

Another group of valuable components found in the endosperm includes the tocotrienols. Grams et al. (1970) discovered that in corn, tocotrienols were found only in the endosperm, whereas the germ contained most of the tocopherols. Tocotrienols can be extracted from plant material using various solvents. Processes for recovering tocotrienols from plant material are described by Lane et al. in U.S. Pat. No. 5,908,940, the entire disclosure of which is incorporated by reference.

Corn oil or corn meal quality is determined by evaluating one or more quality parameters such as the oil yield, phosphorus content, free fatty acid percentage, the neutral starch percentage, protein content, and moisture content. Any known method can be used to calculate one or more of the quality parameters for evaluating the oil or meal quality.

Table 3 displays component amounts for commercially available crude oil and solvent extracted yellow #2 corn oil. The extracted oil obtained from solvent extracted yellow #2 corn has greater amounts of zeazanthin and beta-carotene than does commercially available crude oil obtained from wet or dry milling methods. Conventional crude oil can be obtained from suppliers such as Cargill, Incorporated (Minneapolis, Minn.).

TABLE 3

| Component | Commercially Available Crude Oil | Solvent Extracted Yellow #2 Corn Oil |
|---|---|---|
| Lovibond (Yellow, Red) | —, 14 | 70, 12 |
| Free Fatty Acid | 3.0 | 2.42 |
| Zeazanthin (mg/g) | 0.005 | 5.0 |
| Beta-Carotene (IU/100 g) | 15.5 | 727 |
| Vitamin A (IU/100 g) | 100 | <100 |
| Vitamin $B_6$ (mg/100 g) | 0.400 | — |
| Vitamin $B_{12}$ (mg/100 g) | 0.500 | — |
| Niacin (mg/100 g) | 2.05 | — |
| α-tocopherol (PPM) | 11.88 | 184 |
| β-tocopherol (PPM) | <0.5 | <0.5 |
| γ-tocopherol (PPM) | 29.94 | 311 |
| δ-tocopherol (PPM) | 27.4 | 43 |

TABLE 3-continued

| Component | Commercially Available Crude Oil | Solvent Extracted Yellow #2 Corn Oil |
|---|---|---|
| α-tocotrienol (PPM) | — | 231 |
| β-tocotrienol (PPM) | — | 23 |
| γ-tocotrienol (PPM) | — | 1463 |
| δ-tocotrienol (PPM) | — | 63 |
| C16-palmitic | 10.7 | 10.7 |
| C18-stearate | 1.9 | 1.9 |
| C18:1-9c-oleic | 27.5 | 25.5 |
| C18:2-9c, 12c-linoleic | 57.1 | 58.4 |
| C18:3-9c, 12c, 15c-linolenic | 1.09 | 1.2 |
| Phosphorous (PPM) | 520 | — |
| Folic Acid (mg/100 g) | 25.0 | — |
| Pantothenic Acid (mg/100 g) | 0.250 | — |
| Monoglycerides | — | 0.03 |
| Diglycerides | — | 1.62 |
| Triglycerides | — | 91.36 |
| Hydrocarbons | — | 0.02 |
| Squalane | — | <0.01 |
| Squalene | — | 0.08 |
| Steryl Esters | — | 0.91 |
| Stanol Esters | — | 0.3 |

Oil-based products made with corn oil obtained by the extraction method described herein can contain higher levels of other important nutrients than similar products made with corn oil produced by conventional wet and dry milling processes. The corn oil obtained by the extraction methods described herein will include the corn oil from the germ and endosperm, as well as other components extracted from the whole corn. The other extracted components include such other desirable nutrients as, tocotrienols, tocopherols, carotenoids, carotenes, xanthophylls, and sterols.

Tocopherols (vitamin E) and vitamin A are antioxidants and fat-soluble vitamins. When included in the diet, both have demonstrated health benefits. Blending of oil of the present invention with other oils or substances to achieve an appropriate level of beta-carotene, vitamin E, and tocotrienols is deemed within the scope of the present invention. In some embodiments, extracted corn oil prepared as described herein comprises from about 50 parts per million (ppm) to about 300 ppm of α-tocopherol and from about 1000 ppm to about 3000 ppm of γ-tocotrienol.

Oil produced in accordance with the present invention also may include approximately a 10-fold to a 17-fold increase in tocotrienol content over wet or dry milled crude corn oil. Using the method of optionally tempering, cracking, and/or optionally conditioning, and flaking, the corn oil was extracted and was then analyzed for tocotrienol content. The actual minimum and maximum values for tocotrienol content will depend upon the particular corn used.

The oxidative stability index (OSI), measured in hours, is a measure of an oil's relative stability toward oxidation. Generally, the greater the OSI, the less susceptible the oil is toward oxidation and the longer it takes to oxidize the oil under test or use conditions. In addition, the greater that the content of unsaturated fatty acids is present in the oil, the lower the OSI. Exemplary oils prepared according to the extraction method described herein generally possess OSI values ranging from about 10 hours to about 22 hours.

Extraction of carotenes and xanthophylls and other pigments is described in detail by Blessin (*Cereal Chemistry*, 39, 236–242 (1962); the entire disclosure of which is incorporated by reference). Combinations of solvents, primarily ethanol and hexanes, can be used to extract carotenes and xanthophylls from corn. Ethanol, hexanes, other solvents combinations, and ratios thereof may be used to produce oil of the present invention on a commercial scale.

Exemplary embodiments of the crude oil obtained according to the extraction method described herein generally possess the partial composition profile featured in Table 4.

TABLE 4

| Component | Extracted Whole Corn (Example) (Weight %) | Extracted Whole Corn (Range) (Weight %) |
| --- | --- | --- |
| Free Fatty Acids (FFA) | 2.42 | 0.7–3.00 |
| C16:0 | 10.7 | 9–14 |
| C18:0 | 1.9 | 1.5–3.5 |
| C18:1, cis | 25.5 | 20–40 |
| C18:2, cis | 58.4 | 45–65 |
| C18:3 | 1.2 | 0.6–2.0 |
| Total Tocopherols (ppm) | 1780 | 1000–3000 |

Fatty acids generally found in the corn oil generally include palmitic, stearic, oleic, linoleic and linolenic acids.

The crude oil prepared according to the methods described herein can be subsequently partially or completely hydrogenated. Suitable methods for partially or completely hydrogenating oil are described in D. R. Erickson, Practical Handbook of Soybean Processing Utilization (1995, AOCS Press), the entire disclosure of which is hereby incorporated by reference.

When making oil-based products according to the invention, those products can include conventional corn oil, soy oil, canola oil, olive oil, palm oil, sunflower oil, safflower oil, antioxidant, flavoring, hydrogenated oil, partially hydrogenated oil and/or animal fat. By mixing the corn oil herein with one or more other oils, blended oil products are made. The corn oil-based products can also include materials such as food additives, salt, fat, food colors, □-carotene, annatto extract, curcumin or tumeric, □-apo-8'-carotenal and methyl and ethyl esters thereof, natural or synthetic flavors, antioxidants, propyl gallate, butylated hydroxytoluene, butylated hydroxyanisole, natural or synthetic tocopherols, ascorbyl palmitate, ascorbyl stearate, dilauryl thiodiproprionate, antioxidant synergists, citric acid, sodium citrate, isopropyl citrate, phosphoric acid, monoglyceride citrate, anti-foaming agent, dimethyl polysiloxane, crystallization inhibitor, oxystearin, amino acids, vitamin, minerals, carbohydrates, sugars, herbs, spices, acidity regulators, firming agents, enzyme preparations, flour treatment agents, viscosity control agents, enzymes, lipids, and/or vegetable or animal protein. Additionally, these edible products can be enhanced or enriched with protein supplements containing utilizable protein. An exemplary food product such as a breakfast cereal could include ingredients such as meal of the invention, wheat and oat flour, sugar, salt, corn syrup, milled corn, dried fruit, vitamin C, B vitamins, folic acid, baking soda, and flavorings.

Other exemplary oil-based products that can comprise the oil prepared herein include food oil, cooking oil, edible oil and blended oil.

Equipment used for the extraction of oil from oilseeds, such as soybean and canola, can be used to prepare the corn oil and extracted corn meal described herein. Useful commercial-scale oilseed flakers can be obtained from French Oil Mill Machinery Company, Piqua, Ohio; Roskamp Champion, Waterloo, Iowa; Buhler, based in Switzerland with offices in Plymouth, Minn.; Bauermeister, Inc., Germany; Consolidated Process Machinery Roskamp Company, on the world wide web at http://www.cpmroskamp.com, and Crown Iron Works, Minneapolis, Minn.

Commercial-scale methods and equipment are sufficient for extracting corn oil from at least about 1 ton of corn per day. In some embodiments, the capacity of commercial-scale operations ranges from about 100 tons of corn per day to about 3000 tons of corn per day, or the capacity ranges from about 700 tons of corn per day to about 1700 tons of corn per day. Commercial-scale operations that process greater than about 3000 tons of corn per day are also sufficient.

The phosphorus concentration of crude oil can be determined using AOCS method Ca 12-55. AOCS method Ca 12-55 identifies the phosphorus or the equivalent phosphatide zinc oxide, followed by the spectrophotometric measurement of phosphorus as a blue phosphomolybdic acid complex. AOCS method Ca 12-55 is applicable to crude, degummed, and refined vegetable oils. The phosphorus concentration is converted to phospholipid concentration, i.e., gum concentration, by multiplying the phosphorus concentration by 30. In some embodiments, corn oil produced according to the invention includes about 100–400 ppm of phosphorus.

The free fatty acid percentage of oil can be determined using AOCS method Ca 5a-40. AOCS method Ca 5a-40 identifies the free fatty acids existing in the oils sample. AOCS method Ca 5a-40 is applicable to all crude and refined vegetable oils, marine oils, and animal fats. The neutral oil loss during processing is determined by adding the gum percentage and the free fatty acid percentage together. The amount of free fatty acid obtained in the extracted corn oil will depend upon the amount of fatty acids found within the whole corn from which the oil was extracted. In some embodiments, the free fatty acid content of the extracted oil ranges from about 0.70% to about 3.00 weight %.

Oil color can be determined using AOCS method Cc 13b-45. AOCS method Cc 13b-45 identifies the color of an oil sample by comparing the oil sample with known color characteristics. AOCS method Cc 13b-45 is applicable to fats and oils provided no turbidity is present in the sample. Color values are evaluated qualitatively by visual inspection of the oil. Generally, visual inspection results in an oil being classified as a light oil or a dark oil compared to a known oil color. Color values are quantitated by determining a red color value and a yellow color value using the AOCS method Cc 13b-45. Typically, crude corn oil isolated using conventional dry milling methods has a red color value ranging from about 7 to about 10 and a yellow color value ranging from about 60 to about 70. Corn oils isolated using flaking methods described herein have oil colors that qualitatively are considered light and generally are lighter than crude corn oil derived from wet or dry milling techniques. The yellow color values may range from about 60 to about 70 and red color values may range from about 7 to about 12, as determined by AOCS Method Cc 13b-93.

The extracted corn oil can be used as a raw material for chemical modification, a component of biodegradable material, a component of a blended food product, a component of an edible oil or cooking oil, lubricant or a component thereof, biodiesel or a component thereof, a component of a snack food, and a component of cosmetics. Since the oil obtained by the extraction process herein has one or more components obtained from non-germ parts of the corn kernel, the oil is enhanced. When making blended oils with the extracted oil, the blending can be done before, during or after the extraction process.

Biodiesel can be produced using the extracted corn oil of the invention. Biodiesel is a general term used for a variety of ester-based oxygenated fuels. Biodiesel produced today is a mixture of fatty acid methyl esters produced by methylating refined vegetable oil. Refined oil is preferable to crude oil or spent fryer oil due primarily to the quality of the glycerol by-product. The main drawbacks with previous biodiesel products and related vegetable oil lubricants are low temperature properties and reactivity toward oxidation and polymerization. A preferred biodiesel product comprises a low cloud point, reduced stearic and polyunsaturated fatty acid content, and high oleic acid content. Pour point correlates with low temperature properties and is influenced by the saturated fatty acid content of the oil. Polyunsaturated fatty acids are more susceptible to oxidation and polymerization reactions.

Solvent extracted corn oil corn can be further processed to form lubricants such as by published procedures practiced currently in the industry (see, e.g., U.S. Pat. No. 6,174,501). Meal produced from the flaking and oil extraction process described herein is used to produce unique feed products such as poultry feed, swine feed and ruminant feed. The corn meal used herein has been obtained after extraction of oil from whole kernels of corn, wherein the kernel has not been separated into its constituent part, although the kernel may or may not have been ground, flaked, cracked, chipped, or abraded. The process of removing the oil from corn via extraction serves to concentrate the remaining nutrients such as protein and essential amino acids.

The meal remaining after the oil is removed from the flaked corn by extraction also has significantly improved properties over those of meals produced by wet or dry milling processes. Feed products containing predominantly corn meal produced by extraction require less supplementation with protein from other sources such as soybeans than feed products containing wet or dry mill processed corn grain. The meal, by virtue of the composition arising from the processing method, offers feed manufacturers flexibility to produce feeds that could otherwise not be made. Animal feed rations having unique physical properties such as bulk density, texture, pelletability, and moisture holding capacity and/or unique nutritional properties are created by including the extracted corn meal of the present invention as a component of said rations. The extracted corn meal isolated using flaking and extraction methods as described herein can, on its own, be a low-fat corn meal. Alternatively, it can be used in combination with other corn meals or nutritional components to make feed rations and food products. The extracted corn meal can also be combined with meals made from crops such as soybeans, canola, sunflower, oilseed rape, cotton, and other crops. The extracted corn meal can also be made from genetically modified corn and/or combined with meals made from transgenic oilseed grains to form an enhanced meal or enhanced product.

The extracted corn meal can be provided as a loose product or a pelleted product, optionally in combination with other components. For example, a pelleted product could include the extracted corn meal (by itself or in combination with other components) that has been pelleted and subsequently coated with zein protein. The corn meal can be included in blended meal products that can be provided in loose or pelleted form.

The feed rations prepared with the extracted corn meal will generally meet the dietary and quality standards set forth in the CODEX ALIMENTARIUS or by the National Research Council. The corn meal of the invention will generally comprise the components in the approximate amounts indicated in Table 5 below.

TABLE 5

| Component | Weight % |
| --- | --- |
| Moisture | 5–25 |
| Starch | 60–80 |
| Protein | 7–20 |
| Fat (Oil) | 0.1–2.0 |

When compared to meals made from corn prepared from wet or dry milling processes, the extracted corn meal described herein provides a greater amount of key nutional components (nutrients) such as vitamins, folic, pantothenic acid, lysine, tryptophan, and/or niacin.

The extracted corn meal prepared as described advantageously can be made to contain specific levels of oil and, in particular, specific ratios of oil to protein, of oil to carbohydrate or of oil to protein to carbohydrate. For example, normal corn with 8% protein and 4% oil has a protein:oil ratio of 2.0. Meal produced by extraction to have 10.5% protein and 1.5% oil has a protein:oil ratio of 7.0. This higher ration makes this meal type and products derived therefrom desirable for certain applications such as animal feed and protein purification.

Varying levels of nutrients are required by different animals depending on species, age, and breed. Feed rations comprising different levels of nutrients are made by subjecting the corn to different degrees of extraction, i.e., more oil is removed from the corn by subjecting it to extraction to a greater degree. Therefore, feed rations comprising the extracted corn meal of the invention can be made to include different amounts of fat, protein, and carbohydrates by controlling the extent to which the corn is extracted. Table 6 details the amounts in which the indicated ingredients are present in animal feed rations comprising the extracted corn meal, the specific inclusion range being indicative of exemplary rations in which extracted corn meal is a main ingredient and the general inclusion range being indicative of rations in which one or more other ingredients, for example, carbohydrate-based energy sources such as sorghum, wheat, and/or other cereal grains or their by-products, or other non-cereal grain ingredients, may be included.

TABLE 6

| Ingredient | General Inclusion Range | Exemplary Inclusion Range |
| --- | --- | --- |
| Corn meal described herein | 2–95% | 50–90% |
| Oilseed Meal[1] | 3–35% | 10–30% |
| Meat and Bone Meal | 0–12% | 0–7% |
| Feather Meal | 0–6% | 0–4% |
| Fat | 0–10% | 1–6% |
| Salt | 0.1–0.5% | 0.1–0.5% |
| Lysine | 0–0.4% | 0–0.4% |
| Methionine | 0–0.3% | 0–0.3% |
| Nutrient Premix | 0.01–1.0% | 0.01–1.0% |

[1]Oilseed meal can consist of, but is not limited to, soy, sunflower, canola, cottonseed, and other plant-based meals, which themselves may or may not have been subjected to an oil extraction process.

Meat and bone meal is obtained from suppliers such as Darling International, Inc. (Irving, Tex.). Oilseed meal is obtained from suppliers such as Cargill Oilseeds (Cedar Rapids, Iowa). Feather meal is obtained from suppliers such as Agri Trading Corp., (Hetchinson, Minn.). Amino acids are obtained from suppliers such as DuCoa, (Highland, Ill.).

Feed rations are made by mixing various materials such as grains, seed meals, vitamins, and/or purified amino acids together to form a composite material that meets dietary requirements for protein, energy, fat, vitamins, minerals, and other nutrients. The mixing process can include grinding and blending the components to produce a relatively homogeneous mixture of nutrients. Physical properties of the feed raw materials and of the compounded feed affect the nutritional quality, storability, and overall value of the products. Suitable processes for manufacturing feed rations are disclosed in Feed Manufacturing Technology IV (1994, American Feed Industry Association) and incorporated herein in its entirety.

The extracted corn meal may be somewhat analogous to steam-flaked corn in terms of digestibility of the starch fraction, but may have better digestibility in ruminants by virtue of the processing conditions. As discussed herein, specific oil levels can be achieved in the extracted meal by altering processing conditions.

Many types of animal feed rations can be developed using extracted corn meal of the present type, and for illustration purposes, the following diet types will be described herein: meal made from corn grain wherein the corn grain has an oil content of from about 3% by weight to about 6% by weight and a protein content of about 7.5% by weight, and meal resulting from this corn has an oil content of about 1.5% by weight for use in a hog finishing diet or in a poultry broiler diet.

Extracted corn meal of the present invention has several advantages over normal corn grain when used as an ingredient in aquaculture feed products. In agriculture, pigments such as carotenoids in feed are often deposited in fatty tissue when consumed resulting in an undesirable color. For some aquaculture species, consumer preference is for very light colored tissue. In other species, such as salmon, consumer preference is for a pink or red tissue. An advantage of extracted corn meal in aquaculture diets is that some undesired pigments will be reduced by virtue of the process to produce extracted corn meal; the solvent-soluble pigment compounds (such as carotenoids) are removed from the meal and concentrated in the oil. A second advantage of extracted corn meal over corn dry-milled or wet-milled corn products is the improved protein content and quality, since the oil has been substantially removed from the kernel resulting in a meal product in which the protein has been concentrated. Because the meal is obtained from all portions of the kernel, including most or all of the embryo, the proteins are generally of higher quality and quantity than would be found in extracted corn grits. By including extracted corn meal in aquaculture feeds, it will be possible to raise animals with fewer undesirable pigment compounds in the tissue.

Solvent extracted corn meal is also useful for fermentation-based production of compounds, such as, for example, ethanol, lactic acid, and vitamins. A method of producing a fermentation-based product such as ethanol comprises combining alpha-amylase enzyme and corn meal that remains after the extraction of oil from whole corn. This combination is incubated and at least one additive, for example, glucoamylase or protease, is included to this combination. The combination is subsequently mixed with a micro-organism capable of fermenting a carbon source to produce the fermentation-based product. Solvent extracted corn meal from whole corn can be hydrolyzed to provide soluble sugars. The meal serves as a carbon and nitrogen source for bacterial, fungal, or yeast cultures. Biotin and other vitamins can be produced through the cultivation of microorganisms. Organisms can include *Pseudomonas mutabilis* (ATCC 31014), *Corynebacterium primorioxydans* (ATCC 31015), Arthrobacter species, Gibberella species, Penicillium species, or combinations thereof.

Nutrients used in the cultivation of these and other microorganisms include, for example, starch, glucose, alcohols, ketones, and as a nitrogen source, peptone, corn steep liquor, soybean powder, ammonium chloride, ammonium sulfate, ammonium nitrate, extracted corn meal, or urea. Various salts and trace elements may also be included in media for the culture of microorganisms. The pH of the culture medium is from about 4 to about 9, preferably from about 6 to about 8 and most preferably about 7 for bacterial species. The pH is preferably from about 5 to about 7 for mold or yeast. During cultivation, temperatures are kept between about 10° C. to about 100° C., preferably between about 20° C. to 80° C., more preferably between about 20° C. to about 40° C., and most preferably about 25° C.

Biotin production is described in U.S. Pat. No. 3,859,167, incorporated herein by reference. Cis-tetrahydro-2-oxo-4-n-pentyl-thieno[3,4-d]imidazoline is added to a culture medium containing solvent extracted corn meal and other appropriate identified ingredients in combination with a microbial species capable of forming biotin. In general, the microorganism is cultivated for 1 to 10 days, preferably 1 to 8 days, and more preferably 2 to 7 days, after which time biotin is separated and purified. In one embodiment, to purify biotin, cells are removed from the culture medium, the filtrate is absorbed on activated charcoal, and purified with an ion exchange column. Alternative methods of purification are also used such as crystallization by adjusting the pH of the biotin-contained solution to near its isoelectric point.

Solvent extracted corn meal can also be further processed to produce biodegradable materials. For instance, the meal of the present invention may be incorporated as a thermoplasticising agent. The meal of the invention may be included in the methods described in U.S. Pat. No. 5,320,669, which is incorporated herein by reference. The thermoplastic material is prepared using solvent extracted corn meal, as obtained from the process described herein. In one embodiment, the biodegradable thermoplastic composition prepared using the meal of the present invention is treated with an organic solvent, and/or optionally a cross-linking agent, to link together the starch and protein of the extracted corn grain. The cross-linking agent referred to herein may be any compound capable of linking the starch and the protein, such as, for example, an aldehyde, an acid anhydride or an epoxide. The compositions so formed using the meal of the present invention can be used to make extruded or molded articles that are biodegradable, water-resistant, and/or have a high level of physical strength.

Blended products comprising the extracted corn meal of the present invention and one or more other oilseed meals are made by one or more of the following ways: 1) combining the corn and the other oilseed prior to cracking and/or flaking and subjecting the entire seed mixture to the flaking and extraction process described herein to form a blended meal; 2) combining the corn and the other oilseed after cracking and conditioning, but prior to flaking and subjecting the entire seed mixture to an extraction process as described herein to form a blended meal; 3) combining the corn and the other oilseed after flaking and subjecting the entire seed mixture to the extraction process described herein to form a blended meal; 4) combining the extracted corn meal with extracted or non-extracted other oilseed meal to form a blended meal; or 5) combinations thereof to form a blended meal. At any time during these processes, additional components can be added to the blended meals to form a blended product.

The extracted corn meal can also be used in foodstuffs such as snack food, blended food products, breads, fermentation feedstock, breakfast cereals, thickened food products such canned fruit fillings, puffed or extruded foods, porridge, cardboard and packaging material.

When used in edible products for humans or animals, the extracted corn meal can be combined with other components such as other meal, other oilseed meal, grain, other corn, sorghum, wheat, wheat milled byproducts, barley, tapioca, corn gluten meal, corn gluten feed, bakery byproduct, full fat rice bran, and rice hull.

The extracted corn meal can also be used as a raw material for production of corn protein isolates, for fermentation, or for further chemical processing. In addition to enzymes, such as amylases and proteases, can be added to the meal to help facilitate the breakdown of starch and proteins.

The extracted corn meal is optionally subjected to conventional methods of separating the starch and protein components. Such methods include, for example, dry milling, wet milling, high pressure pumping or cryogenic processes. These and other suitable processes are disclosed in Watson, S. A. & P. E. Ramstad, ed. (1987, Corn: Chemistry and Technology, Ch. 11 and 12, American Association of Cereal Chemist, Inc., St. Paul, Minn.), the disclosure of which is hereby incorporated by reference. Due to the prior removal of oil from the corn meal, the starch and protein components of the extracted corn meal are separated from other components more easily than they would be if the corn oil were not extracted.

Several important quality parameters for the extracted meal include the fat, starch, protein, and moisture content. Methods for evaluating quality parameters of oilseed meals are disclosed in the AOCS methods, the relevant disclosure of which is hereby incorporated by reference. These methods can also be applied to the extracted corn meal prepared as described herein.

Corn meals derived using different methods or isolated at different times are compared by normalizing the meals to a common moisture content. The moisture content of an oilseed protein concentrate, such as a corn meal or whole corn, is determined using AOCS method Ba 2b-82. The crude fiber content of corn meal is determined using AOCS method Ba 6-84. AOCS method Ba 6-84 is useful for grains, meals, flours, feeds and all fiber bearing material from which the fat can be extracted leaving a workable residue. The average crude fiber content for the corn meal of the invention is 2.0%. Crude protein content of corn meal is determined using AOCS method Ba 4e-93 or AOAC 990.03. The starch content of corn meal is determined using the AACC Method 76-11(glucoamylase method). This method may be modified with the following changes: weigh 0.1 g of sample into a culture tube instead of 1 g of sample into an E-flask; and extract free sugar before enzyme digestion.

It is to be understood that the analytical methods provided herein are illustrative examples of useful methods for computing various quality parameters for the oils and meals described herein. Other suitable methods are known and may be used to compute the quality parameters disclosed and claimed herein.

The following examples are included to demonstrate specific embodiments of the invention. It should be appreciated by those of skill in the art that the techniques disclosed in the examples which follow represent techniques discovered by the inventors to effectively function in the practice of the invention, and thus can be considered to constitute exemplary modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Method for Processing Low Oil Corn

This example describes a continuous solvent extraction process. The solvent extraction process consisted fundamentally of four parts: pre-extraction, extraction, meal desolventization, and oil desolventization. These various stages are described in further detail below.

Table 1 shows the values for the parameter targets for each of the pre-extraction steps, tempering, cracking, conditioning, and flaking. These parameter targets represent desired values for operation of the described process. The corn type can be produced in a number of ways including, but not limited to, using corn such as normal yellow #2 corn, wherein the corn has an oil content of from about 3% by weight to about 6% by weight oil; producing grain from a hybrid wherein the grain is between about 3% by weight and about 6% by weight oil; or producing grain from a mixture of plants wherein the grain harvested has a composite oil level of between about 3% by weight and about 6% by weight.

EXAMPLE TABLE 1

| Pre-Extraction Variable | Value |
|---|---|
| Corn Type | A homogeneous or heterogeneous mixture of corn having a composite oil content of between about 3% by weight and about 6% by weight |
| Throughput (kg/h) | 75 |
| Tempering | |
| Tempered Moisture Content of Corn Kernel (%) | 14 ± 0.5 |
| Cracking | |
| Cracking roll feed temperature (° C.) | Ambient (~25° C.) |
| Top cracking roll gap (inches) | Was determined basis 3 mm particle size ~ 0.1 |
| Top, slow cracking roll speed (RPM) | 708 |
| Top roll speed ratio | 1.5 |
| Top roll corrugation | RBV — Sharp to sharp |
| Bottom cracking roll gap (inches) | Was determined basis 3 mm particle size ~ 0.1 |
| Bottom cracking roll speed (RPM) | 708 |
| Bottom roll speed ratio | 1.5 |
| Bottom roll corrugation | RBV — Sharp to sharp |
| Conditioning | |
| Exit temperature (° C.) | 80 ± 5 |
| Exit moisture (%) | 14 ± 0.5 |
| Capacity (kg.) | 100 |
| Indirect (jacket) steam (psig.) | 30–60 (set to maintain exit temperature) |
| Flaking | |
| Flaker gap setting (inches) | ~0.008 |
| Flaker feed temperature (° C.) | 75 ± 5 |

(A) Pre-Extraction

Tempered whole corn was gate fed from a porta-bin to a bucket elevator to the cracking mill. From the cracking mill, cracks (i.e., particles of whole corn) were conveyed to a conditioner, which discharged to an insulated conveyance system. This system consisted of a second bucket elevator (BE1), air mechanical conveyor, heated steam jacketed conveyor (SJC), and chutes connected in series. From the conveyance system, corn cracks were fed to a flaking roll.

Whole corn was tempered to nominally 14.5% moisture by weight by adding water to "as is" moisture corn in a 350 liter Toronto Coppersmithing Toreo Model R-12 ribbon blender. Water was sprayed into the vessel at a rate of 2 liters/hr. After the appropriate amount of water was added, the corn was stirred for another hour then allowed to soak for 24 hours before being tested for moisture.

The tempered corn was then cracked using a Roskamp (Waterloo, Iowa) double stand cracking roll. Both top and bottom rolls were set such that one roll rotated faster than the other. The fast roll on both top and bottom rotated at 1065 revolutions per minute (rpm) with 6 spiral RBV cut corrugations per inch. The slow rolls were cut identically but rotated at 700 rpm. The roll diameters were 9 inches; the roll length was 12 inches. Crack moistures were 13.3 to 15.7%. Cracks of the following average particle size distribution ranges were generated: 15.9% retained by US #4 mesh screens, 39.9% retained by US #6 mesh screens, 27.8% retained by US #8 mesh screens, 6.8% retained by US #10 mesh screens, 4.3% retained by US #18 mesh screens, and 5.3% pass through US #18 mesh screens.

The cracked corn particles were conditioned using a steam jacketed screw conveyor manufactured by Scott Equipment Company (New Prague, Minn.), model TB 1814 Tender Blend 18" screw diameter and 12 feet in length. Three blades swept the perimeter of the inside of the screw. Paddles were approximately 3 inches wide by 4 inches in length. The screw rotated at 4 rotations per minute. The jacketed side of the conveyor was fed 30 psig saturated steam. The exit temperature was monitored and adjusted to 80° C.

Flakes were generated from the cracked corn using a Roskamp (Waterloo, Iowa) 2862 flaking mill. The mill used has 62-inch long and 28-inch wide rolls. The main drive was designed to turn the fast roll at a nominal 300 rpm, and inter-roll drive (IRD) ratio was 8%. Roll pressure was held constant at 500 psig. Flaking exit moistures were in the range of 9.1 to 11.7%. Exit temperatures were in the range from about 60 to about 83° C. Flake thickness ranged from 0.3 to 0.7 mm. The roll gap was set from nominally less than 0.025 to 0.30 mm (less than 0.001–0.012 inches)

(B) Extraction

A continuous, nominal 150 kg/hr. Crown (Roseville, Minn.) model II pilot extractor was used to process the flaked corn. This pilot scale extractor utilized mixed hexanes as a solvent with five (5) counter-current miscella wash zones and a tail wash section. Six-miscella recirculation pumps were utilized. Fresh hexane at 50 to 60° C. was fed in the upper portion of the extractor. The dimensions of the extractor were 29 feet long, 7.8 inches wide, and 4.5 inches deep. Of the total length, 23 feet were wetted and 19.5 feet of that were subjected to wash. The actual feed rates varied from about 50 to about 120 kg/hr. with a nominal average of about 75 kg/hr. The residence time was nominally 60 minutes. The solvent-to-meal ratios were adjusted between about 0.75:1 and about 1.33:1. Full miscella was sent to the oil desolventization system at about 27 to about 34° C.

Example Table 2 shows the values for the parameter targets for each of the extraction steps. These parameter targets represent desired values for operation of the described process.

EXAMPLE TABLE 2

| Extraction Variable | Value |
| --- | --- |
| Corn Type | A homogeneous or heterogeneous mixture of corn having a composite oil content of between about 3% and about 6% by weight |
| Throughput (kg/h) | 75 |
| Extraction | |
| Moisture of feed (%) | 11–13% |
| Feed temperature (° C.) | >50 |
| Residence time (minutes) | 60 |
| Solvent to meal ratio | 1:1 |
| Steam Jacketed Conveyor | |
| Discharge temperature (° C.) | Nominally 50 |
| Vacuum (H$_2$O) | 0.2 |
| Desolventization | |
| Top deck temperature (° C.) | 100 |
| Bottom deck temperature (° C.) | 70 |
| DT vapor temperature (° C.) | >70 |
| Sparge steam rate (kg./hr.) | Set to achieve DT vapor temperature |

(C) Meal Desolventization

Ambient and indirect heat desolventization occurred first in a Schnecken steam jacketed conveyor (SJC). The SJC consisted of a hollow flight screw inside of a steam jacket. It was 12 feet long and 10 inches in diameter. The open flight screw created a tumbling action as it conveyed the extracted material through the conveyor. This ensured that all material was exposed to the heated wall. A pneumatic controller regulated the amount of steam supplied to the jacket. The temperature at the outlet of the conveyor was monitored and used as the basis for the control of steam supplied to the jacket. Vapors from the conveyor are collected in the low vacuum condenser by the slight negative pressure developed by the system fan. A double-deck nominal 100 kg-capacity desolventizer and toaster (DT) with sweep arm agitation was utilized. Dimensions were 36 inches in diameter, 20 inches high per deck. Steam sparge was piped through the top sweep arm only. Meal exit moistures were in the range of 9.4 to 17.7%. Exit temperatures were in the range from 57 to 104° C.

Hexane recovered from the SJC and extractor was condensed, dewatered, and recycled to the extractor.

(D) Oil Desolventization

Oil desolventization was executed using a Rising film evaporator. This unit consisted of sixteen 1.5 cm diameter tubes inside a large jacket. The jacket was filled with steam, which heated the tubes. The extract-laden liquid (normally oil in hexane called miscella) was pumped into the bottom of the tubes. As it traveled up the inside of the tubes, steam heat caused the liquid to boil. The vapors held the liquid against the wall of the tube in a thin, rising film. At the top the liquid and vapor were allowed to separate. The oil flowed into an overflow pipe to the oil stripper, while the vapors were carried over to a condenser. The tubes were under vacuum so that the liquid boiled at a low temperature.

The oil stripper was a disc-and-donut style distillation column. The liquid was spread out in a thin film over a disc, drips down onto a donut and returns back onto a disc. Thus, the oil cascaded down the column. At the same time, steam was injected into the bottom of the stripper. This steam passed over the liquid film removing the solvent remaining in the liquid. A steam jacket to keep the liquid and steam hot surrounded the disc and donut column. The oil stripper was also under vacuum and the vapors (solvent and steam) went to the same condenser as the RFE vapors. The stripping steam went through a demister to remove water droplets before going into the oil stripper.

Hexane recovered from the rising film evaporator and the oil stripper were condensed, dewatered, and recycled to the extractor.

EXAMPLE 2

A Method of Recovering Lighter Particles Generated During a Continuous Solvent Extraction Process for Separating Oil from Corn Having an Oil Content Between 3% and 6%

This example sets forth one method of recovering lighter particles, such as fines, generated during a moisture removal step from corn processed in a manner illustrated in Example 1.

Corn is processed as described in Example 1 (Cracked and flaked or cracked). The product from the whole flaked corn from the flaking process is heated to remove moisture using standard processing equipment such as a Kice (Wichita, Kans.) classifier model A2612. During this moisture removal step an air stream is provided where the velocity of the air stream is controlled. The velocity of the air stream is regulated such that the smaller and lighter particles are carried away in the air stream, hence separating them from the heavier flakes. The lighter particles are then recovered by standard process equipment such as a baghouse. The recovered lighter particles are then introduced into starch-containing product streams for the recovery of starch or are added to the meal stream after solvent has been removed from the meal.

EXAMPLE 3

A Method of Recovering Lighter Particles Generated During the Cracking Step of a Continuous Solvent Extraction Process for Separating Oil from Corn Having an Oil Content Between 3% and 6%

This example sets forth one method of recovering lighter particles, such as fines, generated during the cracking step from corn processed in a manner illustrated in Example 1.

Whole corn kernels are cracked using a standard cracking mill roller such as Roskamp™ (Waterloo, Iowa) model number 6.5. During this cracking step an air stream is provided whereas the velocity of the air stream is controlled. The velocity of the air stream is regulated such that the smaller and lighter particles are carried away in the air stream, hence separating them from the heavier cracks. The lighter particles are then recovered by standard process equipment such as a baghouse. The recovered lighter particles are then introduced into starch-containing product streams for the recovery of starch.

EXAMPLE 4

A Method of Recovering Lighter Particles Generated Before and After the Flaking Process by Means of a Liquid Spray During a Continuous Solvent Extraction Process for Separating Oil from Corn Having an Oil Content Between 3% and 8%

This example sets forth the recovery by means of a liquid spray of fines generated before and after the flaking process from corn processed in a manner illustrated in Example 1. The liquid spray can be a substance that adds value to the resulting meal as well as recovers the value from the fines.

Corn is processed as described in Example 1. The pre-flaking cracked corn and the post-flaking corn flakes are sprayed or misted with water or oil that physically eliminates the lighter, airborne particles. The water source can be pure water, process water, water or oil that has been supplemented with nutritional additives such as vitamins, enzymes or minerals. The oil can be corn oil. The water or oil stream containing the particulates is carried away from the heavier particles in each case and is collected. The particulates are separated from the liquid using standard process equipment such as through centrifugation. The recovered lighter particles are then introduced into starch-containing product streams for the recovery of starch.

EXAMPLE 5

Production of Fermentation-Based Products

This example sets forth the use of solvent extracted corn meal from the current invention as a rich source of starch for fermentation.

(A) Starch Hydrolysis

Solvent extracted corn meal of the present invention prepared as described herein is a rich source of starch for fermentation. One method to provide soluble sugars suitable for fermentation is to hydrolyze starch molecules. Types of enzymes that can be used to convert starch into simple sugars include amylase(s) (e.g., glucoamylase), proteases, cellulase(s) (e.g., xylonase), esterase(s) (e.g., ferulase, acetylesterase) and ligninase(s). The enzymes may be used alone or in combination.

Two samples (i.e., one sample of yellow dent corn grain with an oil content of 3.7%, one sample of yellow dent corn meal having an oil content of 0.3%) were ground to pass through a 1 mm screen using a Retsch Mill. The corn meal sample was obtained from POS Pilot Plant Corporation (Saskatoon, Saskatchewan, Canada). Three hundred grams (300 g) of each sample was combined with 700 ml of water at 99° C.–100° C. comprising 0.5 ml α-amylase and placed in a sealed container. The pH of each mixture was adjusted to 5.9 with base. The mixtures were stirred for 45 min and additional α-amylase enzyme was added.

After an additional 45 min of incubation, the pH of each mixture was adjusted to 4.5 with acid. One-half of one milliliter (0.5 ml) glucoamylase (Optimax 7525) and 0.5 g protease (Fungal Protease 5000) were added to the sample mixtures and incubated with both enzymes at 62° C. for 22–24 h. Throughout the procedure, the degree of starch hydrolysis was monitored by HPLC (Waters 2690 Separations module) using an organic acid column (Aminex HPX-87H Ion Exclusion Column, 300 mm×7.8 mm, Bio Rad).

Total nitrogen content for each sample was determined by Leco 2000 CN. Free amino nitrogen (FAN) was determined by the AOAC method ($15^{th}$ Ed., 1990, p. 735). The amount of dextrose liberated from starch by the milling process and the amount of available nitrogen in the corn samples are set forth in Example Table 3.

EXAMPLE TABLE 3

| Corn Sample | Calculated Initial Dextrose Content (g/L)♣ | Dextrose* (g/L) | Percent Starch Hydrolysis | FAN* (ppm) | Total Nitrogen (ppm)* | Oil Content (wt %) |
|---|---|---|---|---|---|---|
| Yellow Dent Corn Grain | 251.94 | 175.6 | 69.70 | 223.8 | 2992 | 3.5 |
| Yellow Dent Corn Meal | 265.30 | 220.8 | 83.2 | 243.8 | 3392 | |

♣calculated based on starch content and a chemical gain of 1.11
*indicates "as is" values obtained from 30% starch hydrolysate.

(B) Fermentation

The media for fermentations were normalized on a weight basis. Each sample comprised forty-five grams (45 g) of solvent extracted corn meal which had been enzyme-treated in accordance with part (A) of Example 5, above (resulting in starting dextrose concentrations of 133–233 g/L). Each sample was added to its own 125 ml flask. Yeast extract was added at 1 g/L to ensure that nitrogen was not limiting. Cultures were inoculated with 10% inoculum from overnight yeast cultures (a typical Altech ethanol yeast of *Saccharomyces cerevisiae*) and incubations proceeded for 42 h at 30° C. on a rotary shaker at 125 rpm. Dextrose consumption and ethanol production were monitored by HPLC.

Media for fermentations were normalized on a weight basis, targeting an initial fermentable sugar concentration of approximately 180 g/L. Average starting dextrose concentrations for samples containing yellow dent corn grain and yellow dent corn meal are displayed in Example Table 4.

EXAMPLE TABLE 4

| Corn Samples | Starting Dextrose Concentrations |
|---|---|
| Yellow Dent Corn Grain | 168.6 |
| Yellow Dent Corn Meal | 211.5 |

Ethanol productivity is displayed in Table 12. Productivity in these samples dropped after 15 h, however by this time all of the dextrose was exhausted. Ethanol productivity is shown in Example Table 5.

EXAMPLE TABLE 5

| | Ethanol Yield (g EtOH/g sugar) | | | Ethanol Productivity (g/L/h) | | |
|---|---|---|---|---|---|---|
| Fermentation media | 15 h | 24 h | 40 h | 15 h | 24 h | 40 h |
| Yellow Dent Corn Grain | 0.45 | 0.42 | 0.40 | 5.03 | 2.90 | 1.70 |
| Yellow Dent Corn Meal | 0.48 | 0.47 | 0.44 | 5.07 | 4.06 | 2.31 |

Weight Normalization

Weight normalized ethanol productivity is detailed in Example Table 6.

EXAMPLE TABLE 6

| Fermentation Media | Ethanol Productivity (g/L/h) after 24 h |
|---|---|
| Yellow Dent Corn Grain | 2.90 |
| Yellow Dent Corn Meal | 4.06 |

Starch Normalization

Starting dextrose concentrations for yeast cultures were equalized to approximately 120 g/L. The normalized results are shown in Example Table 7.

EXAMPLE TABLE 7

| Fermentation Media: | Ethanol Productivity (g/L/h) after 15 h | Ethanol Productivity (g/L/h) after 24 h |
|---|---|---|
| Yellow Dent Corn Grain | 3.50 | 2.00 |
| Yellow Dent Corn Meal | 2.77 | 2.06 |

Fermentation and Citric Acid Production

This example sets forth the use of extracted corn meal from the current invention as a rich source of starch for the fermentation production of citric acid. The production of citric acid from extracted corn meal involves several steps including starch hydrolysis, as described in Example 5, fermentation, and citric acid recovery.

Once the starch from solvent extracted corn meal is suitably prepared through treatment with enzymes, the solution is filtered and demineralized according to commonly known practices. Resulting sugars are brought to a solids content of about 120 mg/l with demineralized water in a deep-tank fermentation vessel. The deep tank method is also known as the submerged process. In this method the tank is supplied with sterile air, nutrients and a carbon source, (hydrolyzed starch), and inoculated with *Aspergillus niger* spores. Spores of the fungus in a concentration of about 100 spores per liter of culture liquid, which corresponds to an amount of 10 to 15 g of spores per cubic meter ($m^3$) would be added to the nutrient solution and the citric acid production would be carried out by the fungus. Examples of *A. niger* strains are ATCC 1015 described in U.S. Pat. No. 2,492,667, and DSM 5484 described in U.S. Pat. No. 5,081,025.

The incubation of the broth thus inoculated would be carried out at conditions generally known and described for citric acid production, such as continued aeration and temperature control. During the fermentation process, the temperature would be maintained at about 90 degrees F., the pH would be maintained at about 2 to 3 with sodium citrate, and sterile air would be added to maintain about 50% dissolved oxygen content. Fermentation would be carried out until the fermentation broth reaches a reducing sugar content of about 1 g/L, which may require several days to achieve. Two main separation processes can be used in the recovery of citric acid, the Lime-Sulfuric Acid process and the Liquid extraction process. The Lime-Sulfuric Acid method is commonly used and is familiar to those skilled in the art of citric acid production.

What is claimed is:

1. A method for producing fermentation-based products comprising:

(a) combining an enzyme, water, and a corn meal obtained by cracking whole corn with an oil content from about 3% by weight to about 6% by weight, conditioning the cracked corn and extracting an oil from the conditioned corn by solvent extraction to leave the corn meal;

(b) incubating the combination; and (c) mixing the combination with a micro-organism capable of fermenting a carbon source to produce a fermentation-based product.

2. The method of claim 1 wherein the whole corn is flaked during production of the corn meal.

3. The method of claim 1 wherein the enzyme is selected from the group consisting of an amylase, a protease, a cellulase, an esterase and a liginase.

4. The method of claim 3, wherein the enzyme is an amylase.

5. The method of claim 4, wherein the enzyme is glucoamylase.

6. The method of claim 3, wherein the enzyme is a cellulase.

7. The method of claim 6, wherein the cellulase is xylonase.

8. The method of claim 3, wherein the enzyme is an esterase.

9. The method of claim 8, wherein the esterase is selected from the group consisting of ferulase and acetylesterase.

10. The method of claim 3, wherein the enzyme is a protease.

11. The method of claim 3, wherein the enzyme is a liginase.

12. The method of claim 1, wherein the whole corn is tempered prior to extraction of the oil.

13. The method of claim 12, wherein the step of conditioning is after the step of tempering the whole corn.

14. The method of claim 13, wherein the step of cracking is after the step of tempering and before the step of conditioning the whole corn.

15. The method of claim 1, wherein the fermentation-based product is ethanol.

16. The method of claim 1, wherein the fermentation based product is citric acid.

17. The method of claim 1, wherein the extraction is accomplished by extracting corn oil from grain flaked corn using a continuous solvent extraction process.

18. The method of claim 17, wherein the flaked corn remains in contact with the solvent for a time sufficient to extract the desired amount of oil.

19. The method of claim 18, wherein the flaked corn remains in contact with the solvent for at least 10 minutes.

* * * * *